(12) United States Patent
Naghavi et al.

(10) Patent No.: US 8,815,310 B2
(45) Date of Patent: Aug. 26, 2014

(54) COMPOSITIONS FOR BOOSTING METABOLISM, ASSISTING WEIGHT LOSS, AND PROMOTING CARDIOVASCULAR HEALTH

(76) Inventors: Morteza Naghavi, Houston, TX (US); Albert Andrew Yen, Pearland, TX (US); Mortaza Mark Naghavi, Katy, TX (US); Mojtaba Frank Naghavi, Sugar Land, TX (US); Susan Michelle Splering, Richmond, TX (US)

( * ) Notice: Subject to any disclaimer, the term of this patent is extended or adjusted under 35 U.S.C. 154(b) by 48 days.

(21) Appl. No.: 13/346,792

(22) Filed: Jan. 10, 2012

(65) Prior Publication Data

US 2012/0177623 A1     Jul. 12, 2012

Related U.S. Application Data

(60) Provisional application No. 61/460,870, filed on Jan. 10, 2011.

(51) Int. Cl.
| | |
|---|---|
| *A61K 36/82* | (2006.01) |
| *A61K 36/00* | (2006.01) |
| *A61K 31/122* | (2006.01) |
| *A61K 36/704* | (2006.01) |
| *A61K 31/05* | (2006.01) |
| *A61K 31/592* | (2006.01) |
| *A61K 33/24* | (2006.01) |
| *A61K 31/714* | (2006.01) |
| *A61K 36/77* | (2006.01) |

(52) U.S. Cl.
CPC .............. *A61K 36/82* (2013.01); *A61K 31/122* (2013.01); *A61K 36/704* (2013.01); *A61K 31/05* (2013.01); *A61K 31/592* (2013.01); *A61K 33/24* (2013.01); *A61K 31/714* (2013.01); *A61K 36/77* (2013.01)
USPC .......................................... 424/729; 424/725

(58) Field of Classification Search
None
See application file for complete search history.

(56) References Cited

U.S. PATENT DOCUMENTS

| | | | |
|---|---|---|---|
| 6,541,522 B2 * | 4/2003 | Inman et al. ................... | 514/568 |
| 2002/0127285 A1 * | 9/2002 | Xiu ............................... | 424/725 |
| 2005/0261257 A1 * | 11/2005 | Vermeer ........................ | 514/168 |
| 2007/0010426 A1 * | 1/2007 | Mao et al. ......................... | 514/6 |
| 2010/0272710 A1 * | 10/2010 | Rebbaa ........................ | 424/130.1 |
| 2011/0033414 A1 * | 2/2011 | Hennen ......................... | 424/85.1 |
| 2011/0092552 A1 * | 4/2011 | Svensson et al. .............. | 514/356 |

FOREIGN PATENT DOCUMENTS

WO    WO 2006053184 A2 *    5/2006

* cited by examiner

*Primary Examiner* — Chris R Tate
*Assistant Examiner* — Randall Winston
(74) *Attorney, Agent, or Firm* — David McEwing

(57) ABSTRACT

This invention relates to orally ingested compositions for boosting metabolic rate and reducing or controlling levels of cholesterol and triglycerides and improving cardiovascular function, thus preferably assisting with weight loss and promoting cardiovascular health when administered to mammals, including humans.

12 Claims, No Drawings

COMPOSITIONS FOR BOOSTING METABOLISM, ASSISTING WEIGHT LOSS, AND PROMOTING CARDIOVASCULAR HEALTH

RELATED APPLICATIONS

This application claims priority from and incorporates herein by reference Provisional Application Ser. No. 61/460,870 entitled Compositions for Boosting Metabolism and Promoting Cardiovascular Health filed Jan. 10, 2011.

FIELD OF USE

The subject of this disclosure pertains to boosting metabolism, assisting with weight loss, and improving cardiovascular health.

RELATED ART

Prior metabolism boosters do not comprise the composition taught by this disclosure. Also, the metabolism boosters do not improve cardiovascular health.

BACKGROUND OF THE INVENTION

The disclosure relates to compositions for boosting metabolic rate. It is well known that a high resting metabolic rate (RMR) can assist with weight control and weight loss.

The orally ingested compositions of this disclosure contain effective amounts of vitamins, minerals, herbs, fruit extracts, and other natural extracts and do not contain dangerous stimulants like Ephedrine, commonly known as Ma Huang. Other embodiments of the disclosure contain additional compounds which reduce or control levels of cholesterol and triglycerides or promote improved cardiovascular function.

Prior formulations for boosting metabolism fall short of the unique combinations of this disclosure. Unlike other metabolism-boosting formulations, the compositions disclosed herein include components which promote cardiovascular health, such as Vitamin D, coenzyme Q10, trans-resveratrol, red yeast rice and niacin.

DETAILED DESCRIPTION OF THE INVENTION

The compositions described herein are unique combinations of specific vitamins, minerals, herbs, and nutraceutical compounds. A nutraceutical compound is a food or food product that reportedly provides health and medical benefits, including the prevention and treatment of disease. The essential components boost metabolic rate, help control appetite, and assist weight control and weight loss. Other components reduce or control the levels of total cholesterol, low density lipoproteins (LDL), and triglycerides, and may increase high density lipoproteins (HDL), as well. Other components are believed to promote improved cardiovascular function.

One composition contains Vitamin B12, chromium picolinate, trans-resveratrol, green tea extract, guarana, Vitamin D, DHEA or 7-keto DHEA, and coenzyme Q10.

In order to secure the desired result of boosting metabolic rate and assisting with weight control, the composition includes the following components:

Vitamin B12, a vitamin, 100 to 250 mcg, an essential nutrient that speeds metabolism and boosts energy level.

Chromium picolinate, a mineral, 50 to 150 mcg, helps insulin to metabolize fat, turns protein into muscle, and converts sugar into energy. Chromium is reported to reduce insulin resistance and also to help control appetite.

Resveratrol (trans-resveratrol is the active form), approximately 200 to 400 mg of an 8% (weight/weight) extract from *Polygonum cuspidatum* root, a phytoalexin that activates the SiRT1 gene and reportedly has anti-obesity, anti-inflammatory, anti-aging, and anti-cancer properties.

Green tea extract, 100 to 300 mg of a 95% extract standardized to 95% polyphenols, a component which inhibits the enzyme that causes the breakdown of norepinephrine, thus causing an increase in metabolic rate. Green tea extract has also been shown to increase the rate of brown fat metabolism and has been reported to help control appetite.

Guarana, a thermogenic plant extract similar to caffeine that increases metabolic rate without causing adverse cardiovascular effects.

DHEA, the naturally-occurring steroid, dehydroepiandrosterone; or, 7-keto DHEA, a synthesized derivative of DHEA that exhibits the thermogenic characteristic of DHEA without the associated sex hormone stimulating characteristic In order to secure the desired result of promoting improved cardiovascular function or cardiovascular health, the composition includes the following components:

Vitamin D, as cholecalciferol, is the precursor molecule to cholesterol. Low vitamin D levels are associated with increased risk of cardiovascular death and also with obesity, hypertension, glucose intolerance, and metabolic syndrome.

Coenzyme Q10 (CoQ10), also known as ubiquinone, is a vitamin-like substance present in most cells, primarily in the mitochondria. CoQ10 is a component of the electron transport chain and plays an important role in energy generation. CoQ10 helps to maintain a healthy cardiovascular system. There is evidence of CoQ10 deficiency in heart failure. CoQ10 supplementation can help support the heart and the general circulation.

In addition to the key components, an inert filler, rice flour, is included in the composition.

In order to secure the desired result of further boosting metabolic rate, the following additional components may be provided:

Bitter orange (citrus aurantium), an herbal extract that increase metabolic rate without causing adverse cardiovascular effects Other embodiments of the compositions contain the additional nutraceutical compounds that help to control cholesterol or triglyceride levels. These nutraceutical compounds include:

Red yeast rice (rice that has been fermented by the red yeast, *Monascus purpureus*), has been shown to lower blood lipids, including cholesterol and triglycerides, because it contains a substance that inhibits HMG-CoA reductase, the enzyme that is important for the production of cholesterol in the body.

Niacin, or nicotinic acid, an important B vitamin that may raise HDL, also known as "good" cholesterol, by 15 to 35 percent, while also lowering LDL and triglyceride levels. Niacin can make the skin redden and feel warm to the touch ("flushing"), but this flushing is not harmful.

Omega-3 fish oil, a class of essential polyunsaturated fatty acids found in high concentrations in salmon, halibut, sardines, albacore, and other fatty fishes, has been shown to lower total cholesterol and triglyceride levels, when ingested. Moreover, daily ingestion of omega-3-fatty acids has been linked to prevention of sudden cardiac death in patients who recently survived a heart attack (GISSI-Prevention trial, Circulation, 2002; 105: 1897-1903).

Phytosterols, also called plant sterols, are phytochemicals naturally occurring in plants. Phytosterols have cholesterol-lowering properties, by reducing cholesterol absorption in intestines (Ostlund et al., Am J Clin Nutr, 2003; 77:1385-1589).

Liquid—Solid Combination. In an embodiment, the compositions described herein, which contain only solid components, are packaged with other compositions that are contained in a liquid form. There are various nutraceutical and pharmaceutical compounds that cannot be chemically combined or physically mixed with each other due to factors such as instability of ingredients, insolubility, viscosity, incompatibility, taste, and reduced shelf life. For example, oil-based liquid products such as fish oil will not mix well with water-based liquids. However, it is often desirable to ingest these compounds at or close to the same time. Therefore, there is a need for a means of enabling a person to store or carry these chemically- or physically-incompatible compounds together so that they may be conveniently ingested together when so desired.

"Polyceutical" Combination. In an embodiment, the compositions described herein, which contain only nutraceutical components, are packaged with pharmaceutical compositions. The inventors have coined the term "Polyceutical" to name the combination of one or more nutraceutical compounds with one or more pharmaceutical compounds, i.e., defined as any chemical substance intended for use in the medical diagnosis, cure, treatment, or prevention of disease.

Examples of polyceuticals are: a combination of vitamin B6 and aspirin; a combination of vitamin B12 and aspirin; a combination of folic acid and aspirin; a combination of CoQ10 and ibuprofen; a combination of one of the nutraceutical compositions described in this disclosure and metformin (an oral antidiabetic drug in the biguanide class); and a combination of one of the nutraceutical compositions described in this disclosure and exenatide (a medication approved for the treatment of diabetes mellitus type 2 belonging to the group of incretin mimetics and administered as a subcutaneous injection).

A polyceutical combination is an effective means of providing two or more compounds that have complementary effects. For example, a polyceutical combination for assisting weight loss can combine a nutraceutical composition that boosts metabolism with a pharmaceutical compound that suppresses appetite, such as the FDA-approved prescription weight loss medication, phentermine. Another example, a polyceutical combination for improving cardiovascular health, can combine a nutraceutical composition that raises HDL ("good") cholesterol with a statin medication, e.g., atorvastatin, which lowers LDL ("bad") cholesterol.

The disclosure also includes a system and method for a metabolism boosting and cardiovascular wellness management program. This program may comprise the following steps:

Measure resting metabolic rate, using an indirect calorimeter (such as Microlife's BodyGem®).

Perform baseline assessment of cardiovascular health by measurement of blood pressure, advanced blood lipoprotein fraction analysis, vascular function, and an imaging study of atherosclerosis such as ultrasound measurement of carotid artery intima-media thickness (CIMT).

Regular administration of one or more of the compositions described in this application.

Participation in a regular exercise regimen that includes both aerobic and weight resistance components and is supervised by a personal fitness trainer.

Remote coaching of program participants occurs through Internet-based communications (emails) and text messages to PDAs, smart phones and tablet computers.

At predetermined intervals, repeat measurements of metabolic rate and cardiovascular markers.

Adjust amount and/or type of administered compositions based on the measured changes in metabolic rate and cardiovascular markers.

This specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

What is claimed is:

1. A metabolism boosting composition comprising:
a) 100 to 250 mcg Vitamin B12, or cyanocobalamin;
b) 500 to 1000 IU Vitamin D, or cholecalciferol;
c) 50 to 150 mcg Chromium picolinate;
d) 200 to 400 mg trans-Resveratrol contained within an 8% (wt/wt) extract of *Polygonum cuspidatum* root;
e) 50 to 200 mg DHEA or 7-Keto DHEA;
f) 100 to 300 mg Green tea extract, 95% extract standardized to 95% polyphenols;
g) 25 to 75 mg Guarana 10% extract standardized to 10% caffeine; and
h) 5 to 20 mg Coenzyme Q10.

2. The composition of claim 1 further comprising 0.1 to 0.5 g rice flour.

3. The composition of claim 1 further comprising 400 to 500 mg Bitter Orange extract (6% synephrine).

4. The composition of claim 1 further comprising 100 to 200 mg Niacin.

5. The composition of claim 1 further comprising 400 to 600 mg Red yeast rice.

6. The composition of claim 1 further comprising 500 to 2000 mg Omega-3 fish oil powder.

7. The composition of claim 1 further comprising 2000 to 3000 mg phytosterols.

8. The composition of claim 1 packaged with other compositions that are contained in a liquid form.

9. The composition of claim 1 packaged with one or more pharmaceutical compounds, as a polyceutical combination.

10. A cardiovascular health-promoting composition, packaged as a combination of multi-component and single-component capsules, comprising:
a) 100 to 250 mcg Vitamin B12, or cyanocobalamin;
b) 500 to 1000 IU Vitamin D, or cholecalciferol;
c) 50 to 150 mcg Chromium picolinate;

d) 200 to 400 mg trans-Resveratrol contained within an 8% (wt/wt) extract of *Polygonum cuspidatum* root;
e) 50 to 200 mg DHEA or 7-Keto DHEA;
f) 100 to 300 mg Green tea extract, 95% extract standardized to 95% polyphenols;
g) 25 to 75 mg Guarana 10% extract standardized to 10% caffeine;
h) 5 to 20 mg Coenzyme Q10;
i) 400 to 600 mg Red yeast rice;
j) 100 to 200 mg Niacin;
k) 500 to 2000 mg Omega-3 fish oil powder; and
l) 2000 to 3000 mg phytosterols.

11. The composition of claim 10 packaged with other compositions that are contained in a liquid form.

12. The composition of claim 10 packaged with one or more pharmaceutical compounds, as a polyceutical combination.

* * * * *